United States Patent [19]

Richter et al.

[11] Patent Number: 4,518,761

[45] Date of Patent: May 21, 1985

[54] PROCESS FOR THE PREPARATION OF MIXED TRIMERS FROM ORGANIC ISOCYANATES, THE MIXED TRIMERS OBTAINED ACCORDING TO THE PROCESS AND THE USE THEREOF FOR THE PRODUCTION OF POLYURETHANES

[75] Inventors: Roland Richter, Leverkusen; Hanns P. Müller, Odenthal; Kuno Wagner, Leverkusen; Bernd Riberi, Cologne; Jürg Fröhlich, Burscheid, all of Fed. Rep. of Germany

[73] Assignee: Bayer Aktiengesellschaft, Leverkusen, Fed. Rep. of Germany

[21] Appl. No.: 439,086

[22] Filed: Nov. 4, 1982

[30] Foreign Application Priority Data

Nov. 10, 1981 [DE] Fed. Rep. of Germany ....... 3144672

[51] Int. Cl.$^3$ ................. C08G 18/70; C07D 251/34
[52] U.S. Cl. ..................................... 528/67; 528/48; 528/45; 544/193; 544/221; 544/223
[58] Field of Search ............................ 528/67, 45, 48; 544/222, 221, 193

[56] References Cited

U.S. PATENT DOCUMENTS

| 3,394,111 | 7/1968 | Liebsch et al. | 260/77.5 |
| 3,622,577 | 11/1971 | Pederson | 260/248 NS |
| 3,645,979 | 2/1972 | Liebsch et al. | 260/77.5 NC |
| 3,919,218 | 11/1975 | Schmitt et al. | 260/248 NS |
| 4,031,040 | 6/1977 | Cotter et al. | 528/48 X |
| 4,038,239 | 7/1977 | Coyner et al. | 528/67 X |
| 4,111,914 | 9/1978 | Kresta et al. | 528/48 |
| 4,115,373 | 9/1978 | Henes et al. | 528/48 |
| 4,252,923 | 2/1981 | König et al. | 525/452 |
| 4,255,569 | 3/1981 | Müller et al. | 544/193 |
| 4,379,905 | 4/1983 | Stemmler et al. | 544/222 X |
| 4,419,513 | 12/1983 | Breidenbach et al. | 544/222 |

FOREIGN PATENT DOCUMENTS 1112243 11/1981 Canada .
3100262 1/1981 Fed. Rep. of Germany .
949253 2/1964 United Kingdom .
1244416 9/1971 United Kingdom .

OTHER PUBLICATIONS

*Polyurethanes, Chemistry and Technology*, Part I, Saunders & Frisch, 1962, Interscience Publishers, (p. 1).
Advances in Catalysis, vol. 13, 393, (1962), B. A. Farkas & G. A. Mills.
Org. Coat., Plast. Chem. 42 516, (1980), J. E. Kresta, K. H. Hsieh.
European Polymer Journal, vol. 17, p. 35, (1981), S. Dabi and A. Zilkha.
Chemical Abstracts, vol. 94, 1981, p. 83, No. 158365y.

Primary Examiner—John Kight
Assistant Examiner—Garnette D. Draper
Attorney, Agent, or Firm—Gene Harsh; Joseph C. Gil; Thomas W. Roy

[57] ABSTRACT

The present invention is directed to a new process for the preparation of mixed trimers by at least partly trimerizing the isocyanate groups of at least two organic isocyanates of a reactivity which differs in the sense of the trimerization reaction, in the presence of trimerization catalysts and optionally interrupting the trimerization reaction at the respectively desired degree of trimerization, in which process the less reactive isocyanate component is introduced, polymerization is then commenced in the presence of the catalyst with the trimerization of at least 0.1% of the isocyanate groups and the more reactive isocyanate component is finally metered into the reaction mixture thus obtained; the mixed trimers obtained according to this process; and the use of the mixed trimers having free isocyanate groups obtained by this process, optionally in a form blocked by blocking agents for organic polyisocyanates, as a starting material for the production of polyurethane plastics materials.

10 Claims, No Drawings

PROCESS FOR THE PREPARATION OF MIXED TRIMERS FROM ORGANIC ISOCYANATES, THE MIXED TRIMERS OBTAINED ACCORDING TO THE PROCESS AND THE USE THEREOF FOR THE PRODUCTION OF POLYURETHANES

BACKGROUND OF THE INVENTION

1. Field of the Invention

This invention relates to a new process for the preparation of mixed trimers from organic isocyanates of a reactivity which differs insofar as the isocyanate trimerization reaction is concerned, to the mixed trimers obtained according to the process and to the use of the mixed trimers obtained according to the process, containing free isocyanate groups, optionally in a form blocked by blocking agents for isocyanate groups, for the production of polyurethane plastics.

2. Description of the Prior Art

Processes for trimerizing organic isocyanates are known (see, for example, B. A. Farkas, G. A. Mills, *Advances in Catalysis*, Vol. 13, 393 (1962); J. H. Saunders, K. C. Frisch, *Polyurethanes, Chemistry and Technology*, Interscience Publishers, New York (1962); J. E. Kresta, K. H. Hsieh, *Org. Coat, Plast. Chem.*, 42, 516 (1980); German Offenlegungsschrift Nos. 1,201,992; 1,954,093; 2,325,826; 2,551,634; 2,641,380; 2,644,684; 2,726,749 and 2,901,479; British Pat. No. 949,253; Published European Patent Application Nos. 9694 and 10589; U.S. Pat. No. 3,622,577 or German Patent Application Nos. 3,100,262.5 or 3,100,263.3).

The preparation of mixed trimers from aromatic and aliphatic diisocyanates is described, for example, in German Pat. No. 1,670,667. For this purpose, mixtures of hexamethylene diisocyanate and 2,4-diisocyanatotoluene, for example, are partly trimerized in the presence of organic phosphines as the trimerization catalyst, during which operation, however, the aliphatic diisocyanate is incorporated into the trimer to a much smaller extent than that which corresponds to its concentration in the starting mixture. Thus, the aliphatic isocyanates are used simultaneously in the process of this prior publication not so much with the objective of preparing mixed trimers, but rather due to the cocatalytic influence of the aliphatic diisocyanate on the phosphine-catalyzed trimerization of aromatic diisocyanates. In spite of this co-catalytic effect of the aliphatic diisocyanate, considerable quantities of non-trimerized aromatic starting diisocyanates are still always present in the reaction mixtures described by the prior publication after terminating the trimerization reaction so that while recovering the unreacted diisocyanates their separation into the aliphatic and aromatic starting diisocyanates is necessary. Another disadvantage of the process described in German Pat. No. 1,670,667 is seen in the essential use of organic phosphines as trimerization catalysts. Since organic phosphines are primarily dimerization catalysts for organic diisocyanates, the trimerization reaction in the process of German Pat. No. 1,670,667 presumably also takes place via the intermediate stage of dimers (uretdiones). Moreover, the formation of mixed trimers in the process of the prior publication can only be explained based on this specific reaction mechanism. During the trimerization of mixtures of isocyanates of different reactivity with other trimerization catalysts which do not form uretdiones, homotrimers of the aromatic diisocyanates are mostly produced because the aliphatic diisocyanates which are slower to react only participate in the trimerization reaction after a certain degree of dilution of the aromatic diisocyanates is reached. Accordingly, mixed trimers only form to a slight extent while aromatic and aliphatic homotrimers are preferably formed. Pure mixed trimers are only produced during the trimerization of isocyanate mixtures when mixtures of isocyanates having essentially chemically equivalent NCO groups are trimerized. Thus, for example, the two aromatic monoisocyanates, 4-chlorophenylisocyanate and 3,4-dichlorophenylisocyanate, may be mix-trimerized with suitable catalysts, the proportion of mixed trimer being determined by the composition of the mixture.

In *European Polymer Journal*, Vol. 17, page 35 (1981), S. Dabi and A. Zilkha have recently described a specific type of catalyst, tributyl tin oxide, for the mixed trimerization of less frequently used mono- and diisocyanates; however, the process which is recommended requires temperatures of above 100° C. and a proportion of catalyst greater than 1% by weight, which greatly impairs the quality of the resulting products and rules out a commercial use, in particular, for the polyurethane lacquer area. Moreover, uretdiones are also formed as by-products with this type of catalyst.

The object of the present invention is to provide a general preparation process, according to which pure mixed trimers are obtained as the main product in one step from any mixtures of isocyanates of differing reactivity using a catalyst. The process conditions should be similar to those of the prior art for the homo-trimerization of polyisocyanates into polyisocyanates containing isocyanurate groups because the resulting products are preferably used for the production of polyurethane plastics. However, a commercial possibility of using the mixed trimers containing isocyanate groups is only provided (1) if the proportion of catalyst is small enough that it may easily be deactivated and optionally separated, (2) if the thermal strain is so low that no disadvantageous discolorations of the products occur and (3) if no uretdiones are formed as by-products because the toxicologically harmful monomeric isocyanates could be produced therefrom during storage as a result of splitting back.

Surprisingly, it has now been found that this object may be achieved by the process according to the present invention which is described in more detail in the following, and in which (1) the isocyanate which is slower to react is introduced in excess, (2) is mixed with a quantity of catalyst sufficient for the trimerization thereof, (3) trimerization of the solution is started for a short time and (4) the more reactive isocyanate is then continuously added to the slower-reacting activated isocyanate. In the process according to the present invention, more than about 50% and preferably more than about 70% of pure mixed trimers are produced based on the total quantity of the resulting trimers, and the proportion of the isocyanates of lower or higher reactivity which are incorporated in the mixed trimer may be simply controlled by the rate of adding the isocyanate component of higher reactivity and by the total ratio of (isocyanate component of lower reactivity):(isocyanate component of higher reactivity).

SUMMARY OF THE INVENTION

The present invention is directed to a process for the preparation of mixed trimers by at least partially trimerizing the isocyanate groups of two isocyanate components with different reactivities in the sense of the trimerization reaction in the presence of a trimerization catalyst which comprises (a) adding the less reactive isocyanate component to a reaction vessel, (b) trimerizing at least about 0.1% of the isocyanate groups of said less reactive isocyanate component in the presence of a trimerization catalyst, (c) metering the more reactive isocyanate component into said reaction vessel and, optionally, (d) terminating the trimerization reaction at the desired degree of trimerization by thermal decomposition of said trimerization catalyst and/or by adding a catalyst poison.

The present invention also relates to the mixed trimers obtained according to this process.

The invention additionally relates to the use of the mixed trimers obtained according to this process and having free isocyanate groups, optionally in a form blocked by blocking agents for organic polyisocyanates, as a starting material for the production of polyurethane plastics according to the isocyanate-polyaddition process.

DETAILED DESCRIPTION OF THE INVENTION

In the process according to the present invention, two isocyanate components are used as starting materials wherein each component comprises at least one isocyanate, and the isocyanate groups of both components have differing reactivities in trimerization reactions. This condition, which is essential to the present invention, is met when the same parts by weight of the respective isocyanate components are reacted to the same degree of trimerization at the same starting temperature for the same reaction time and when using a 1:1 complex of potassium acetate and 18-Crown-6, differ at least by a factor of 2 with respect to the concentration of catalyst necessary for this purpose. Thus, two simple preliminary tests may simply be carried out to check whether this condition essential to the present invention has been met.

The term "degree of trimerization" as used herein is understood to mean the percentage of the isocyanate groups present in the starting isocyanates which have completely reacted during the trimerization reaction with the formation of isocyanurate groups. If, in the present process, isocyanate mixtures are used as isocyanate component (a) having isocyanate groups of a comparatively low reactivity and/or as isocyanate component (b) having isocyanate groups of a comparatively higher reactivity, the condition which has been mentioned with respect to the different reactivity between the isocyanate of component b) having the highest reactivity and the isocyanate of component a) having the lowest reactivity must be met.

The condition mentioned with respect to the different reactivities is generally always met when isocyanates having aliphatic and/or cycloaliphatic isocyanate groups on the one hand and isocyanates having aromatically bound isocyanate groups on the other hand are used. Thus, combinations of this type are preferably used in the process according to the present invention. These isocyanates are preferably those of the following formula:

$$Q(NCO)_n$$

wherein

Q represents an aliphatic hydrocarbon radical having from 1 to 18 carbon atoms, a cycloaliphatic hydrocarbon radical having from 3 to 15 carbon atoms, an araliphatic hydrocarbon radical having from 7 to 20 carbon atoms or an optionally methyl-substituted, aromatic hydrocarbon radical having a total of from 6 to 15 carbon atoms, and n represents an integer from 1 to 4.

The araliphatic isocyanates are also isocyanates having aliphatically bound isocyanate groups.

Typical examples of isocyanates having aliphatically bound isocyanate groups include the following: methyl isocyanate, ethyl isocyanate, propyl isocyanate, n-butyl isocyanate, tert.-butyl isocyanate, isohexyl isocyanate, dodecyl isocyanate, oleyl isocyanate, stearyl isocyanate, cyclohexyl isocyanate, benzyl isocyanate, α-methylbenzyl isocyanate, phenylethyl isocyanate, triphenylmethyl isocyanate, tetramethylene diisocyanate, hexamethylene diisocyanate, nonamethylene diisocyanate, 5-methyl-nonamethylene diisocyanate, 1,4-xylylene diisocyanate, 1,3-xylylene diisocyanate, ω,ω'-diisocyanato-1,4-diethylbenzene, cyclobutane-1,3-diisocyanate, cyclohexane-1,4-diisocyanate, cyclohexane-1,3-diisocyanate, di-(4-isocyanatocyclohexyl)-methane, 1-isocyanato-3-isocyanatomethyl-3,5,5-trimethylcyclohexane, 2,2,4-trimethyl-hexamethylene diisocyanate, 2,4,4-trimethyl-hexamethylene diisocyanate, 1,12-dodecane diisocyanate, 1,6,11-triisocyanato-undecane, 2,4- or 2,6-hexahydrotoluylene diisocyanate, 1,3- or 1,4-hexahydrophenylene diisocyanate, 1,3-butadienylene-1,4-diisocyanate, or 2,4'-perhydro-diphenylmethane diisocyanate.

Typical examples of isocyanates which are suitable according to the present invention and have aromatically bound isocyanate groups include the following: phenyl isocyanate, 4-, 3- or 2-methylphenyl isocyanate, 1-naphthyl isocyanate, 1,3- or 1,4-phenylene diisocyanate, 2,4- or 2,6-toluylene diisocyanate, 2,4'-diphenylmethane diisocyanate, 4,4'-diphenylmethane diisocyanate, naphthylene-1,5-diisocyanate, 4,4',4"-triisocyanato-triphenylmethane, 2,4,6-triisocyanatotoluene or polyphenyl-polymethylene-polyisocyanates as prepared by aniline-formaldehyde condensation and subsequent phosgenation ("crude MDI").

However, in addition to these starting isocyanates corresponding to the above general formula, isocyanates which are interrupted and/or substituted by hetero atoms and have aliphatic or aromatically bound isocyanate groups or heteroaromatic isocyanates may also be used in the present process. Examples of these substances include the following: 2-chloroethyl isocyanate, 2-cyanoethyl isocyanate, 6-chlorohexyl isocyanate, isocyanatoacetic acid ethyl ester, propyletherpropyl isocyanate, 3-methoxypropyl isocyanate, 2-(2-methoxyethoxy)-ethyl isocyanate, 3,6,9-trioxadecyl isocyanate, allyl isocyanate, 1,3-pentadienyl isocyanate, 1,2-ethylene diisocyanate, ω,ω'-diisocyanato-n-propylether; lysine methyl ester diisocyanate, lysine-(2-isocyanato ethyl ester)-diisocyanate, 4- or 3-chlorophenyl isocyanate, 3,4-, 2,3-, 2,4-, 2,5- or 2,6-dichlorophenyl isocyanate, 2,4,5- or 2,4,6-trichlorophenyl isocyanate, 4-, 3- or 2-nitrophenyl isocyanate, 2,5-dichloro-4-nitrophenyl isocyanate, 2,4-dichloro-6-nitrophenyl isocyanate, 2,6-dichloro-4-nitrophenyl isocyanate, 3- or 2-chloro-4-nitrophenyl isocyanate, 2-chloro-5-nitrophenyl isocyanate, 4-chloro-3- or 2-nitrophenyl isocyanate, 5-chloro-2-nitrophenyl isocyanate, 4-trichloro-, tribromo- or trifluoromethylphenyl isocyanate, 3-chloro-4-trifluoromethylphenyl isocyanate, 3-trifluoromethylphenyl isocyanate, 3-chloro-4-methylphenyl isocyanate, 4-methoxyphenyl isocyanate, 4-trichloro-, tribromo- or trifluoromethoxyphenyl isocyanate, 4-methylmercaptophenyl isocyanate, 4-trichloro-, tribromo- or trifluoromethylmercaptophenyl isocyanate, 4-(1,1,2-trifluoro-2-chloroethane mercapto)-phenyl isocyanate, 4-(1,1,2-trifluoro-2-chloroethoxy)-phenyl isocyanate, 4-phenoxyphenyl isocyanate, 4-(4'-chlorophenoxy)phenyl isocyanate, 4-(3'-trifluoromethylphenoxy)-phenyl isocyanate, tris-(4-isocyanatophenyl)-orthophosphoric acid, 2-isocyanato-3,4,5,6-tetrachloropyridine, 2-isocyanato-4,5,6-trichloropyrimidine, 6-isocyanato-2,4,5-trichloropyrimidine, 6-isocyanato-4,5-dichloro-2-trichloromethylpyrimidine, 2-isocyanato-3,5,6-trichloropyridazine, 4,6-dichloro-s-triazinyl isocyanate and 6-chloro-s-triazinylene diisocyanate.

The process according to the present invention is not restricted to the use of combinations of isocyanates having aliphatically or cycloaliphatically bound isocyanate groups on the one hand and isocyanates having aromatically bound isocyanate groups on the other hand. Instead, the only condition essential to the invention of different reactivity may also be met when, for example, isocyanates having aliphatically or cycloaliphatically bound isocyanate groups on the one hand are combined with isocyanates having heteroaromatically bound isocyanate groups on the other hand. However, the essential condition of different reactivity may also be met when only isocyanates having aliphatically and/or cycloaliphatically bound isocyanate groups or only isocyanates having aromatically or heteroaromatically bound isocyanate groups are used, provided the different reactivity of the isocyanate groups, due to the presence of steric effects (combinations of sterically unhindered isocyanates with isocyanates having sterically hindered isocyanate groups), is ensured by activating or deactivating substituents (for example, combinations of electron-attracting substituents, such as aromatic groups substituted with trifluoromethyl groups, nitro groups or halogen atoms with unsubstituted or alkyl- or alkoxy-substituted aromatic isocyanates) and/or by the type of bond of the isocyanate groups (for example, combinations of aliphatic isocyanates, the isocyanate groups of which are bound to primary carbon atoms, with aliphatic isocyanates, the isocyanate groups of which are bound to secondary or tertiary carbon atoms). Thus, for example, the following combinations also meet the condition essential to the invention with respect to different reactivity (the first-mentioned isocyanate is the more reactive in each case): phenylisocyanate/p-trifluoromethoxyphenyl isocyanate; p-trifluoromethylphenyl isocyanate/p-trifluoromethylmercaptophenyl isocyanate; allyl isocyanate/butyl isocyanate; allyl isocyanate/hexamethylene diisocyanate; hexamethylene diisocyanate/di-(4-isocyanatocyclohexyl)-methane; hexamethylene diisocyanate/3,6,9-trioxadecyl isocyanate; 1,3-pentadienyl isocyanate/1-isocyanato-3-isocyanatomethyl-3,5,5-trimethylcyclohexane; and 6-chloro-s-triazinylene diisocyanate/2,4-toluylene diisocyanate.

Aliphatic or cycloaliphatic diisocyanates of the type mentioned by way of example which do not have any heteroatoms in addition to the isocyanate groups are most preferably used in the present process as isocyanates of a comparatively low reactivity, and optionally methyl-substituted, aromatic diisocyanates which, apart from the isocyanate groups, do not have any other heteroatoms are most preferably used as isocyanates of a comparatively high reactivity.

Any prior art trimerization catalysts may be used as the trimerization catalysts, for example, those disclosed in the above-mentioned publications, provided that the catalyst is active enough to trimerize the isocyanate which is slower to react at temperatures of below about 100° C. Phosphine-free catalysts are preferably used.

During the preparation of isocyanate group-free mixed trimers from monoisocyanates, it is unimportant whether the catalyst is deactivated thermally or by adding a catalyst poison, because it is unnecessary in this case to terminate the trimerization reaction. During the preparation of trimers containing isocyanate groups, using polyisocyanates, in particular diisocyanates, the trimerization reaction must be terminated in a known manner at the respectively required degree of trimerization by thermal decomposition and/or by adding a catalyst poison. In this case, the use of suitable catalysts is, of course, necessary.

The following are included as particularly well suited catalysts:

(a) 1:1 complexes of (i) basic sodium or potassium compounds and (ii) 1,4,7,10,13-pentaoxacyclopentadecane ("15-Crown-5") or 1,4,7,10,13,16-hexaoxacyclooxadecane ("18-Crown-6"). In this context, the term "1:1-complexes" is understood to mean complexes of equimolar quantities of a basic sodium or potassium compound with 15-Crown-5 or 18-Crown-6. The sodium compounds are preferably complexed with the first-mentioned cyclic polyethers and the potassium compounds are preferably complexed with the last-mentioned cyclic polyethers.

Any compounds of the alkali metals mentioned, the aqueous solution of which has a pH of at least 7.5 in one-molar concentration, are included as basic sodium or potassium compounds. Suitable basic compounds include, for example, sodium or potassium carboxylates preferably having from 1 to 12 carbon atoms, sodium or potassium alcoholates preferably having from 1 to 8 carbon atoms, sodium or potassium phenolates preferably having from 6 to 10 carbon atoms, and sodium or potassium carbonates, hydroxides, cyanates, enolates or cyanides. Suitable basic sodium or potassium compounds include, for example, the formates, acetates, propionates, 2-ethylhexanoates, n-dodecanoates, caprylates, methylates, ethylates, butylates, hexylates, phenolates, tert.butylphenolates, carbonates, hydroxides, cyanates, thiocyanates, or cyanides of the metals mentioned or also sodium or potassium-N-methylacetamide, for example. The carboxylates, alcoholates, phenolates, carbonates, hydroxides cyanates and cyanides mentioned are included among the preferred basic compounds. Single carboxylates of the alkali metals mentioned having from 1 to 4 carbon atoms, in particular potassium acetate, are particularly preferred.

The cyclic polyethers used for the complex formation are known compounds. They may be prepared, for example, according to G. Johns, C. J. Ransom and C. B. Reese, in *Synthesis*, (1976), page 515.

The 1:1 complexes may be prepared, for example, according to one of the following methods:

1. The complexes are prepared using the isocyanate to be trimerized or the solution thereof in a suitable solvent which may also be used as a reaction medium when carrying out the process according to the present invention, such that the cyclic polyether is dissolved in the isocyanate of lower reactivity or in the solution thereof and the alkali metal salt is stirred in as a solid with complex formation and dissolving.

2. The cyclic polyether is dissolved in a suitable solvent and thereafter the alkali metal salt is metered in with complex formation and dissolving. Possible clouding is removed by filtration.

3. The process is carried out as described under 2, but using a relatively readily volatile solvent which is drawn off after the complex formation, so that the complex is produced as a solid residue which is then dissolved in another solvent and/or in the isocyanate of lower reactivity.

During the preparation of the 1:1-complexes, the components (i) and (ii) are preferably used in equimolar quantities. Of course, it would also be possible to work with other quantity ratios which, however, would mean that either the basic alkali metal compound or the cyclic polyether would be present in excess. As may easily be comprehended, a method of this type would not be very appropriate, because the respective excess would not have a catalytic effect or would only have a comparatively low catalytic effect. During the preparation of solutions of the 1:1-complexes, the components (i) and (ii) are generally used in such quantities that from about 0.4 to 40%, preferably from about 0.8 to 20%, by weight solutions of the complexes are present. It is just one of the major advantages of the catalysts that they are soluble in the solvents exemplified in the following, in such comparatively high concentrations.

Solvents which, as indicated above, may optionally also be used as a reaction medium for the preparation of the complexes are particularly the polar, essentially physiologically harmless solvents which are conventional in polyurethane lacquer technology having a boiling point at normal pressure of from about 50 to 350° C., or compounds which are liquid at room temperature and have alcoholic hydroxyl groups and a molecular weight of from about 32 to 250, preferably from about 46 to 162. Of course, any mixtures of such solvents may also be used. Examples of suitable solvents of the type mentioned include the following: ethyl acetate, butyl acetate, ethylglycol acetate, acetone, methylethyl ketone, methylisobutyl ketone, cyclohexanone, methoxy-hexanone, or chlorohydrocarbons, for example, chloroform or chlorobenzene. There is a restricted solubility with diluents such as, for example, toluene, xylene and higher aromatics. If greater quantities of such solvents are added, clouding and precipitation may result. Examples of compounds suitable as solvents and having alcoholic hydroxyl groups include the following: methanol, ethanol, isopropanol, ethylene glycol acetate, ethylene glycol, diethylene glycol, ethylene glycol monoethylether, glycerine or trimethylolpropane. Since the 1:1-complexes are generally very soluble in such compounds containing hydroxyl groups, such that the alcoholic solvents only have to be used in very low quantities, the presence thereof does not disturb the process according to the present invention.

In addition to these solvents mentioned, higher boiling solvents may also be used, for example, the conventional plasticizers such as dibutyl phthalate, butylbenzyl phthalate or phosphoric acid esters such as tricresylphosphate.

(b) Complexes of (i) basic alkali metal compounds of the type mentioned and (iii) acyclic organic compounds which contain:

(1) at least 5 alkylene oxide units of the formula

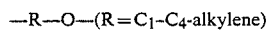

in the form of one or more polyether chains having at least 3 alkylene oxide units, (2) altogether at least about 40% by weight of alkylene oxide units of the type mentioned positioned in polyether chains and which (3) have a molecular weight of at least about 238.

In this case, as opposed to the cyclic compounds (ii) mentioned above, the catalyst components (iii) are acyclic organic compounds which meet the above-mentioned criteria, in particular such compounds which contain:

(1) at least 5 alkylene oxide units of the type mentioned, preferably ethylene oxide and optionally propylene oxide units in the form of one or more polyether chains having, respectively, at least 3 preferably, respectively, at least 5, alkylene oxide units, (2) at least about 55% by weight of alkylene oxide units of the type mentioned incorporated inside polyether chains, at least about 50%, preferably at least about 80%, of all present alkylene oxide units being ethylene oxide units, and which (3) have a molecular weight of from about 238 to 3000, most preferably from about 266 to 1000.

While chains having less than three alkylene oxide units may be present, they are not counted when determining the total number of alkylene oxide units under (1). In addition, they are not counted as alkylene oxide units when determining the weight percent of alkylene oxide units under (2).

Typical examples of suitable catalyst components (iii) are mono- to trihydric polyether alcohols corresponding to these definitions, as they may be obtained in a known manner by alkoxylating, in particular by ethoxylating, suitable starting molecules, such as monohydric alcohols, for example, methanol, ethanol, n-or i-propanol, n-, i-, sec.- or tert.-butanol, water or at least divalent starting molecules such as ethylene glycol, propanediol-(1,2), propanediol-(1,3), butane-, pentane- or hexanediols, glycerine, trimethylolethane or trimethylolpropane. Those polyethers of the type mentioned by way of example are also suitable when the terminally-positioned hydroxyl group(s) have been blocked, for example, by alkylation, acylation and/or urethanization, so that terminal groups having reactivities comparable to the reactivity of hydroxyl groups with isocyanate groups are no longer present. Also suitable are the derivatives of the polyether alcohols mentioned which have been chain-lengthened by a reaction with chain-lengthening agents, for example, diisocyanates such as tetramethylene diisocyanate, hexamethylene diisocyanate or 2,4-diisocyanatotoluene, as far as the derivatives thus obtained correspond to the above definitions.

The terminally-positioned hydroxyl group(s) of the polyether alcohols mentioned above by way of example are blocked by alkylation by reacting the polyether alcohols with alkylating agents, for example, dimethyl sulfate, $C_1$–$C_4$-alkyl halide or benzyl halide. Blocking by an acylation reaction takes place by a reaction with acylating agents such as acetic acid anhydride, acetyl chloride or benzoyl chloride. Blocking by urethanization takes place by a reaction with monovalent isocyanates such as methyl, ethyl, hexyl or phenyl isocyanate. By reacting the polyether alcohols mentioned by way of example with aldehydes such as formaldehyde, acetaldehyde or benzaldehyde in an acetalization reaction, optionally substituted methylene oxide units are introduced into the polyether.

In order to prepare these complexes to be used as trimerization catalysts, the components (i) and (iii) mentioned by way of example or any of the mixtures thereof are reacted with each other in such quantity ratios that from about 0.8 to 2.0, preferably from about 1.0 to 1.5 mols of compounds (iii) corresponding to the above definitions are available per gram equivalent of basic metal compound (i). If, during the preparation of the complexes, alkoxylation products of the starting molecules mentioned by way of example or of the derivatives thereof are used which are mixtures, due to the alkoxylation reaction taking place statistically, which mixtures, in addition to the compounds (iii) corresponding to the above definitions, also contain compounds which do not correspond to these definitions, for example, due to too small a content of alkylene oxide units, the quantity of such mixtures must, of course, be calculated such that the above quantity ratios of the components (i) and (iii) are observed. The reaction between the components (i) and (iii), i.e., the complex formation, generally takes place spontaneously at a temperature of from about 10° to 60° C., in particular when mutually compatible components (i) and (iii) are used in the absence of solvents. However, the complexes may also be formed in the presence of solvents or solvent mixtures of the type mentioned by way of example above.

If the components (i) and (iii) are mutually compatible and/or are readily soluble in the solvent used, the mixture of (i) and (iii) or the solutions thereof may be used immediately after their preparation as trimerization catalysts. It is also possible in this case to meter the components (i) and (iii) separately into the isocyanate of comparatively low reactivity to be trimerized, although this is a less preferred measure. However, if the components (i) and (iii) are mutually incompatible and are insoluble or only sparingly soluble in the solvent used, it is often appropriate to mechanically intermix the initially formed suspensions for about 15 to 360 minutes within the temperature range specified and to filter off any possibly remaining deposit. The solution of the complex which is then present may be used as such or concentrated under vacuum. The remaining solvent-free complex may finally be dissolved in other, preferably aprotic solvents. Thus, for example, about 0.02 molar "solutions of potassium acetate" may be prepared in toluene at room temperature.

When carrying out the process according to the present invention, the strict absence of alcohol in solvents for the complexes or of complex formers (iii) containing hydroxyl groups does not have to be observed, because the extremely small quantities under discussion are negligible compared to the isocyanate groups of the starting polyisocyanate to be trimerized.

The process according to the present invention may be carried out solvent-free or in the presence of any organic solvents which are inert to isocyanate groups and, for the starting isocyanates, are a solvent of the type mentioned above in the description of the preferred catalysts.

When carrying out the process of the present invention, the ratio of the isocyanate component (a) having isocyanate groups of comparatively low reactivity to the isocyanate component (b) having isocyanate groups of comparatively high reactivity is calculated such that there is an NCO equivalent ratio of (a):(b) of from about 1:1 to 10:1, preferably from about 2:1 to 8:1. In the method of preparation, the isocyanate component (a) is introduced at from about 10° to 100° C., preferably from about 20° to 50° C., and is then mixed with the quantity of catalyst which is just sufficient for the start of trimerization. In the case of the particularly preferred complexed alkali metal compounds, this quantity is generally from about 0.005 to 0.5, preferably from about 0.001 to 0.1% by weight, based on complexing agent-free, alkali metal compounds on the one hand and on isocyanate component (a) on the other hand. As soon as the exothermic trimerization reaction has resulted in a degree of trimerization of from about 0.1 to 8%, preferably from about 0.5 to 5%, the reactive isocyanate component (b) is continuously added such that the reaction constantly remains exothermic at from about 30° to 100° C., preferably from about 50° to 70° C. The temperature of the reaction is controlled via the addition rate and by suitable cooling measures. After the addition, the mixture is further stirred until the required degree of trimerization is reached and the reaction is then stopped by inhibiting the catalyst.

However, as already explained, it is unnecessary to stop the trimerization reaction when isocyanate group-free trimers are being prepared from monoisocyanates. In the case of thermally labile trimerization catalysts, for example, in the case of using quaternary ammonium hydroxides having hydroxyalkyl substituents, the catalyst is deactivated thermally by a short temperature shock, but preferably by adding a catalyst poison. When the particularly preferred complexed alkali metal compounds are used, acid chlorides, in particular are suitable, such as benzoylchloride, acetylchloride, succinic acid dichloride, terephthalic acid dichloride, 2,5-dichlorobenzoic acid chloride, phosphorus trichloride or thionyl chloride, or strong acids such as p-toluene sulfonic acid, nonafluorobutane sulfonic acid or phosphoric acid and carbamic acid chlorides, which may be formed by the addition of HCl to isocyanates. The catalyst poisons deactivate the catalysts essential to this invention by neutralizing the basic alkali metal compounds.

When trimers having isocyanate groups are prepared, the reaction is generally stopped before a degree of trimerization of about 50%, preferably about 30% is reached, based on the total quantity of the isocyanates used. There are generally no longer any isocyanates (b) having isocyanate groups of comparatively high reactivity then present in the reaction mixture, so that in addition to the product of the process, only the isocyanate component (a) having isocyanate groups of comparatively low reactivity are present in the mixture. The excess starting isocyanate may then be separated from the product of the process, if required, by extraction or preferably by distillation, in particular in a thin layer evaporator.

The products of the process according to the present invention having free isocyanate groups are valuable starting materials for the production of polyurethane plastics materials according to the isocyanate polyaddition process, i.e., by reaction with compounds containing isocyanate-reactive hydrogens. They may be used for this purpose in a known manner in a free form as well as in a form blocked by blocking agents for isocyanate groups. The isocyanate group-free products of the process of this invention which are based on monoisocyanates are new compounds which may be used as biologically effective substances.

In the following Examples, all the percentages are based on weight. The products which are described are identified and characterized by the combined use of mass spectrometry, high pressure liquid chromatography, gas chromatography and gel chromatography.

EXAMPLES

EXAMPLE 1

Testing for different reactivity (a) 100 g of 2,4-toluylene diisocyanate (NCO content 48.25%) are mixed at 25° C. with 7.4 mg (0.02 mmol) of a 1:1-complex of potassium acetate and 18-Crown-6 dissolved in 1 ml of 2-ethylhexanol. After 45 minutes and a heat of reaction of 90° C., the NCO content is 38.4%. This corresponds to a degree of trimerization of 20%.

(b) 100 g of hexamethylene diisocyanate (NCO content 49.96%) are mixed at 25° C. with 185 mg (0.51 mmol) of a 1:1-complex of potassium acetate and 18-Crown-6 dissolved in 1 ml of 2-ethylhexanol. After 45 minutes and a heat of reaction of 65° C., the NCO content is 40.0%. This corresponds to a degree of trimerization of 20%.

The condition essential to this invention of different reactivity is met because the necessary concentration of catalyst differs by a factor of 25.

EXAMPLE 2 (Comparison)

348 g of 2,4-toluylene diisocyanate (TDI) and 168 g of hexamethylene diisocyanate (HDI) are mixed with 0.15 mmol of a 1:1-complex of potassium acetate and 18-Crown-6 at 25° C. and with the exclusion of moisture. The reaction mixture heats itself to 58° C. over a period of 35 minutes, and thereafter the temperature is maintained at 50° C. by additional heating. After stirring for 4 hours, the NCO content has fallen to 38.7% and the reaction is stopped by adding 0.15 mmol of benzoyl chloride. The product cannot be thin-layer distilled, because crystallization immediately occurs in the column. A molecular mass of 522 (pure TDI trimer) is found exclusively in the reaction product as monomeric isocyanurate. The monomeric isocyanates' portion contains 47.3% of TDI and 52.7% of HDI.

EXAMPLE 3 (Comparison)

168 g of HDI and 87 g of TDI are mixed at 25° C. with 0.5 ml of a 0.5 molar solution of potassium acetate in polyethylene glycol (average molecular weight 370). The reaction mixture heats itself to 69° C. over a period of 25 minutes. After 32 minutes, the temperature is 63° C. and the NCO content has fallen to 38.0%. The reaction is then stopped by adding 0.25 mmol of benzoyl chloride. The reaction product behaves like the product of Comparative Example 2; it cannot be thin-layer distilled. When distilled at 0.5 mbar on a rotary evaporator (bath temperature 200° C.), 97 g of a crystalline residue are obtained which mainly only contain pure TDI trimer (molecular weight 522) as monomeric isocyanurate. In the distillate (156 g), the proportion of HDI is 95%.

The two Comparative Examples 2 and 3 show that independently of the mixing ratio, the trimerization of a mixture of HDI and TDI produces substantially pure TDI trimer. About 10 to 30% of HDI are also incorporated only in the higher molecular weight oligomers.

EXAMPLE 4 (According to the present invention)

500 g of hexamethylene diisocyanate (HDI) are mixed with 1.0 ml of a 0.5 molar solution of potassium acetate in polyethylene glycol (average molecular weight 370; catalyst concentration =0.01% of potassium acetate based on HDI), at 25° C. with stirring and with the exclusion of moisture. After 15 minutes, the NCO content is 48.8% (degree of trimerization=2.3%) and the reaction temperature is 40° C. 100 g of 2,4-toluylene diisocyanate (TDI) are then added dropwise continuously over a period of 40 minutes, the temperature slowly rising to 52° C. After the addition, the NCO content is 41.6%. The reaction is stopped by adding 0.25 mmol of hexamethylenedicarbamic acid chloride (HDI x 2 HCl). After thin-layer distillation (vacuum 0.8 mbar, circulatory temperature 180° C., free TDI in the distillate 4%), 148 g of a slightly yellowish colored product is obtained which, mixed with butyl acetate (60% solids content), has an NCO content of 11.7%, a viscosity (25° C.) of 505 mPas and a monomer content HDI/TDI<0.2%. The proportion of TDI in the trimer is 48%; however, the homotrimers of the molecular masses 504 (3 HDI) and 552 (3 TDI) together only make up from 5 to 10%. A molecular mass of 510 (1 TDI/2 HDI) as well as molecular mass of 516 (2 TDI/1 HDI) are found for the monoisocyanurates.

EXAMPLE 5 (According to the present invention)

504 g of hexamethylene diisocyanate (HDI) are mixed with 5 ml of a 0.2 molar solution of potassium acetate/18-Crown-6 (1:1) in diethylene glycol monomethylether (=0.02% potassium acetate based on HDI) at 25° C. with stirring. After 4 minutes, the reaction temperature is 30° C. 174 g of 2,4-toluylene diisocyanate (TDI) are then added dropwise continuously over a period of 45 minutes, the temperature being maintained at from 50° to 70° C. by occasional cooling. After the addition, the NCO content is 37.6%. After a further 5 minutes, the NCO content has fallen to 37% and the reaction is stopped by adding 1 mmol of nonafluorobutane sulfonic acid. After thin-layer distillation (free TDI in the distillate 0.6%), 287 g of a slightly yellowish resin is obtained having an NCO content of 17.4%, a content of monomeric HDI of 0.19% and a content of monomeric TDI of 0.1%. The TDI proportion in the product is 57%. All the theoretically possible molecular masses are again found for the monoisocyanurates: 504, 510, 516 and 522, with the proportion of the homotrimers amounting to less than 20%. The gel chromatogram shows that, in addition to the monoisocyanurates (about 30%), higher branched oligomers, such as diisocyanurates (about 20%), tri-, tetra- and pentaisocyanurates (about 30%) and about 20% of isocyanurates linked together having a molecular mass >2500 are present.

EXAMPLE 6 (According to the present invention)

2016 g of hexamethylene diisocyanate (HDI) are mixed with 7.0 ml of a 0.5 molar solution of potassium acetate in polyethylene glycol (average molecular weight 370; catalyst concentration =0.017% potassium acetate based on HDI) at 25° C., with stirring and the exclusion of moisture. After 10 minutes, the reaction temperature is 35° C. 696 g of 2,4-toluylene diisocyanate (TDI) are then added dropwise continuously over a period of 50 minutes, the temperature being maintained at from 40° to 50° C. by occasional cooling. After the addition, the NCO content is 36.0% and the temperature is 45° C. The mixture is stirred for a further 10 minutes until the NCO content has fallen to 35.2% and the reaction is then stopped by adding 3 mmol of benzoyl chloride. After thin layer distillation, 1362 g of distillate are obtained in which there are 0.3% of TDI, and 1297 g of trimer having an NCO content of 18.0% and a content of free HDI/TDI of 0.15%. The proportion of incorporated TDI is 51%. TDI homotrimer is only formed in traces.

EXAMPLE 7 (Comparison)

30 g of phenyl isocyanate and 105 g of hexylmethylene diisocyanate (HDI) are mixed at 25° C. with 0.6 ml of a 0.5 molar solution of potassium acetate in polyethylene glycol (average molecular weight 370); 0.03% of potassium acetate based on HDI. The solution heats itself to 70° C. over a period of 30 minutes and then has an NCO content of 29%. After a further 30 minutes, the temperature has again fallen to 25° C. and a crystalline product is deposited. The NCO content has not decreased further. After diluting with toluene, and after filtering and recrystallization from glacial acetic acid, 60% of phenyl isocyanurate is obtained, melting point 274° C.

EXAMPLE 8 (According to the present invention)

252 g of hexamethylene diisocyanate (HDI) are mixed with 1.25 ml of a 0.5 molar solution of potassium acetate in polyethylene glycol (average molecular weight 370; catalyst concentration =0.025% of potassium acetate based on HDI) at 25° C. and with stirring. After 30 minutes, the reaction temperature is 40° C. 60 g of phenyl isocyanate are then added dropwise continuously over a period of 135 minutes, the temperature being maintained at from 60° to 80° C. by cooling. After the addition, the NCO content of the clear solution is 19.6% and the reaction is interrupted by adding 0.6 mmol of nonafluorobutane sulfonic acid. After thin-layer distillation (free phenyl isocyanate in the distillate <0.1%), a viscous, slightly yellowish product is obtained having an NCO content of 13.1% and a content of free HDI of 0.15%. The product is composed of the monoisocyanurates of the molecular masses 406 (2 PI/1 HDI), 455 (1 PI/2 HDI), 504 (3 HDI), and a little 357 (3 PI).

Moreover, in addition to higher molecular weight oligomers, it also produces trimerization products of the following general formula:

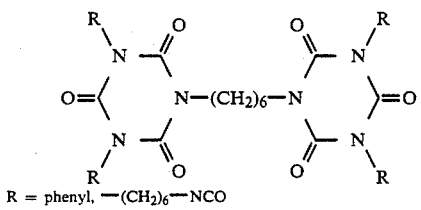

R = phenyl, —(CH$_2$)$_6$—NCO and all the theoretically possible molecular masses (644, 693, 742, 791 and 840) are present.

EXAMPLE 9 (According to the present invention)

504 g of hexamethylene diisocyanate (HDI) are mixed with 1.5 ml of a 0.5 molar solution of potassium acetate in polyethylene glycol (average molecular weight 370; catalyst concentration=0.015% of potassium acetate based on HDI) at 25° C., with stirring and the exclusion of moisture. After 20 minutes, the reaction temperature is 40° C. Molten 4,4'-diisocyanatodiphenylmethane (MDI) is then added dropwise continuously over a period of 35 minutes, the temperature being maintained at from 50 to 70° C. by occasional cooling. After the addition, the mixture is further stirred for another 10 minutes until the NCO content amounts to 28.0%. The reaction is then stopped by adding 0.7 mmol of nonafluorobutane sulfonic acid. After thin-layer distillation (free MDI in the distillate 0.2%), 430 g of a colorless viscous product is obtained having an NCO content of 16.0%, a content of free HDI of 0.18% and a content of free MDI of 0.4%. The mixed trimer of the following formula:

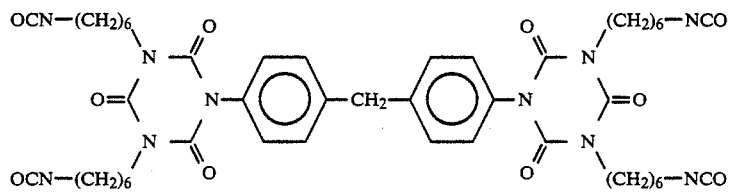

is in the product, in addition to the monoisocyanurates of molecular mass 504 (3 HDI), 586 (2 HDI/1 MDI) and 668 (1 HDI/2 MDI) and higher molecular weight oligomers. The proportion of incorporated MDI amounts to 29%.

EXAMPLE 10 (Comparison)

(a) 5 ml of a 0.02 molar solution of potassium acetate/18-Crown-6 (1:1) in butyl acetate are added to 10 g of phenyl isocyanate, dissolved in 15 ml of toluene. The reaction mixture heats itself to 100° C. over a period of 2 minutes and all the phenyl isocyanate has trimerized.

(b) 12.5 ml of a 0.02 molar solution of potassium acetate/18-Crown-6 (1:1) in butyl acetate are added to 10 g of p-trifluoromethoxyphenyl isocyanate dissolved in 7.5 ml of toluene. All the isocyanate has trimerized over a period of 2 hours and the temperature rises to 53° C.

(c) 5 ml of a 0.02 molar solution of potassium acetate/18-Crown-6 (1:1) inbutyl acetate are added at 25° C. to 11.5 g of p-trifluoromethoxyphenyl isocyanate and 5.0 g of phenyl isocyanate which are dissolved in 15 ml of toluene. All the isocyanate has finished reacting over a period of 6 hours and 30 minutes, the temperature rising to 40° C. in the meantime. After filtering the solids, 7.7 g (67%) of trifluoromethoxyphenyl isocyanurate are obtained. Phenyl isocyanurate and 1,3-(di-p-trifluoromethoxyphenyl)-5-phenyl-1,3,5-triazine-2,4,6[1H, 3H, 5H]-trione are found in the filtrate. 3,5-diphenyl-1-(p-trifluoromethoxyphenyl)-1,3,5-triazine-2,4,6-(1H, 3H, 5H)-trione cannot be detected.

EXAMPLE 11 (According to the present invention)

11.5 g of p-trifluoromethoxyphenyl isocyanate are dissolved in 10 ml of toluene and are mixed at 25° C.

with 10 ml of a 0.02 molar solution of potassium acetate/18-Crown-6 (1:1) in butyl acetate. After the reaction mixture has heated itself to 30° C., 5.0 g of phenyl isocyanate are added over a period of 5 minutes and the mixture is stirred until all the isocyanate has reacted. After separating by column chromatography, the two mixed isocyanurates 1,3-(di-p-trifluoromethoxyphenyl)-5-phenyl-1,3,5-triazine-2,4,6(1H,3H,5H)-trione and 3,5-diphenyl-1-(p-trifluoromethoxyphenyl)-1,3,5-triazine-2,4,6(1H,3H,5H)-trione are obtained in a 73% yield.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of mixed trimers by at least partially trimerizing the isocyanate groups of two isocyanate components with different reactivities in the sense of the trimerization reaction in the presence of a trimerization catalyst which comprises
    (a) adding the less reactive isocyanate component to a reaction vessel,
    (b) trimerizing at least about 0.1% of the isocyanate groups of said less reactive isocyanate component in the presence of a trimerization catalyst,
    (c) metering the more reactive isocyanate component into said reaction vessel and, optionally,
    (d) terminating the trimerization reaction at the desired degree of trimerization by thermal decomposition of said trimerization catalyst and/or by adding a catalyst poison.

2. The process according to claim 1 which comprises metering said more reactive isocyanate component into said reaction vessel when from about 0.5 to 5% of the isocyanate groups of said less reactive isocyanate component have been trimerized.

3. The process according to claim 1 characterized in that a phosphine-free trimerization catalyst is used as said trimerization catalyst.

4. The process according to claim 2 or 3, characterized in that organic isocyanates having aliphatically and/or cycloaliphatically bound isocyanate groups are used as said less reactive isocyanate component and organic isocyanates having aromatically bound isocyanate groups are used as said more reactive isocyanate component.

5. The process according to claim 4, characterized in that organic diisocyanates are used as the starting isocyanates.

6. The process according to claim 2 or 3 which comprises terminating the trimerization reaction by thermally decomposing the trimerization catalyst and/or by adding a catalyst poison before 50% of the total isocyanate groups present in the reaction vessel are in a trimerized form.

7. The process according to claim 6 which comprises separating the unreacted starting isocyanate in the reaction vessel by distillation or extraction after terminating the trimerization reaction.

8. The product as produced by the process of claim 2 or 3.

9. A process for the preparation of polyurethanes by the isocyanate polyaddition reaction which comprises
    (a) preparing mixed trimers containing free isocyanate groups by the process of claim 2 or 3 and
    (b) subsequently reacting said mixed trimers with compounds containing isocyanate-reactive hydrogens.

10. The process of claim 9 wherein the free isocyanate groups of component (a) are blocked with blocking agents for isocyanate groups.

* * * * *